United States Patent [19]

Terada

[11] 4,253,448

[45] Mar. 3, 1981

[54] ENDOSCOPE CONNECTOR

[75] Inventor: Masaaki Terada, Hachioji, Japan

[73] Assignee: Olympus Optical Co., Ltd., Tokyo, Japan

[21] Appl. No.: 77,471

[22] Filed: Sep. 20, 1979

[30] Foreign Application Priority Data

Sep. 29, 1978 [JP] Japan .................. 53-120161

[51] Int. Cl.³ .............................. A61B 1/00
[52] U.S. Cl. ........................... 128/4; 128/6
[58] Field of Search ............... 128/6, 4, 5, 7, 8, 247

[56] References Cited

U.S. PATENT DOCUMENTS

| | | | |
|---|---|---|---|
| 3,726,272 | 4/1973 | Fukami et al. | 128/6 |
| 3,830,225 | 8/1974 | Shinnick | 128/4 |
| 3,958,566 | 5/1976 | Furihata | 128/4 |

Primary Examiner—John D. Yasko

[57] ABSTRACT

An endoscope connector comprises a socket member which has a cylindrical penetrating bore, that portion of said socket member at which one end of the penetrating bore is opened being connected to a console containing a light source and a connection for an electric source, and whose peripheral wall is provided with a fluid-feeding fitting and suction fitting; a cylindrical plug member which is sealingly inserted into the cylindrical penetrating bore of the socket member to rotate around the axis, receives the distal end portions of an illumination optical fiber bundle, fluid-feeding tube and suction tube extending from an endoscope, said plug member having one end which is near the other end of the socket member and to which the free end of a protection tube receiving the illumination optical fiber bundle, fluid-feeding tube and suction tube is fixed; and a pair of annular chambers which are formed between the surface of the cylindrical penetrating bore of the socket member and the peripheral surface of the plug member, and one of which communicates with the fluid-feeding fitting and fluid-feeding tube, and the other of which communicates with the suction fitting and suction tube.

9 Claims, 8 Drawing Figures

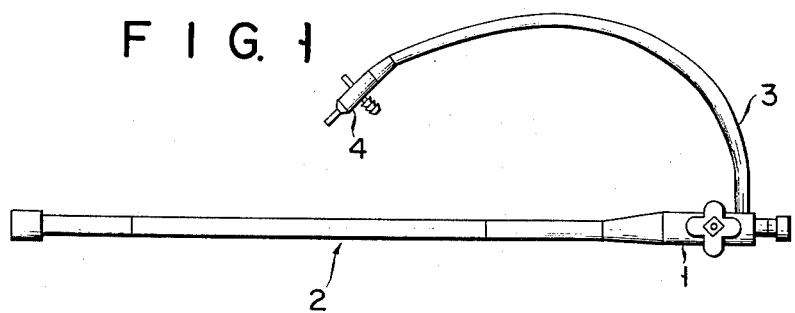
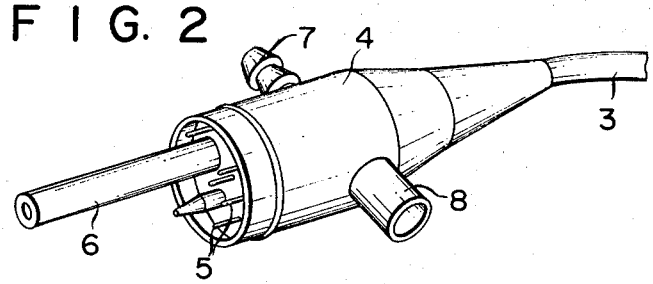
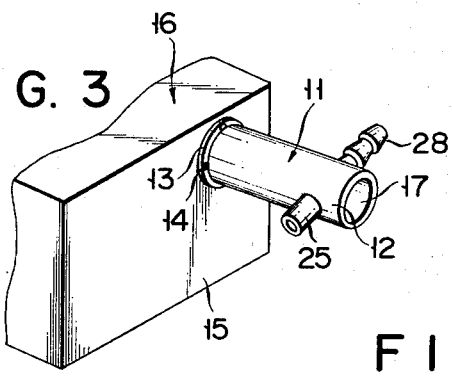
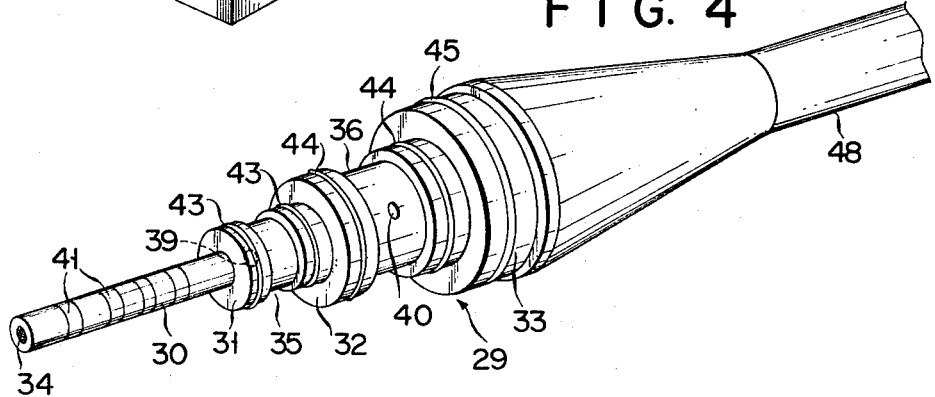

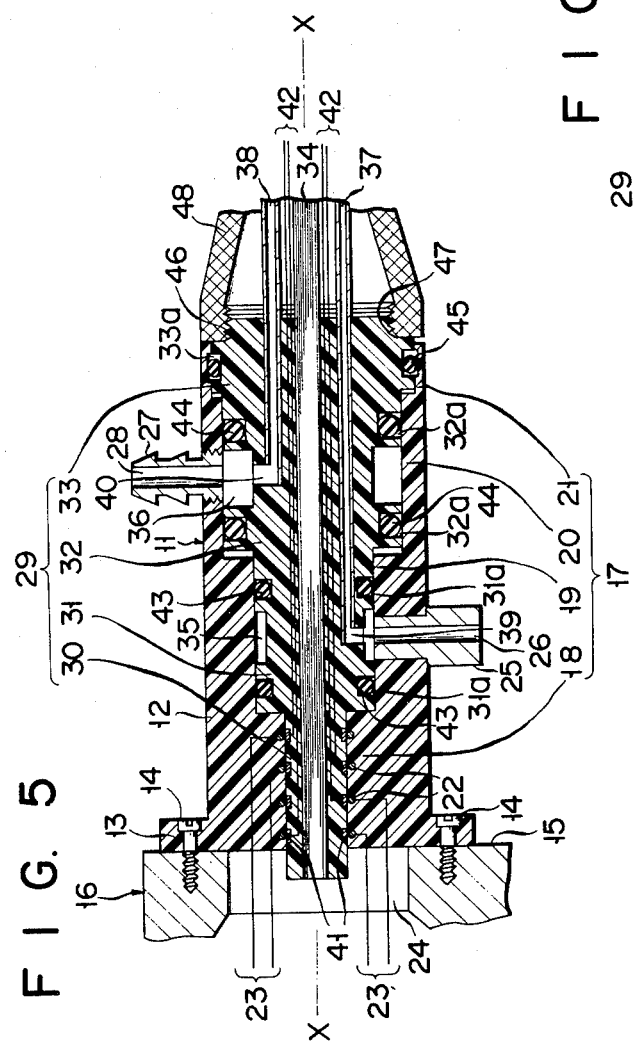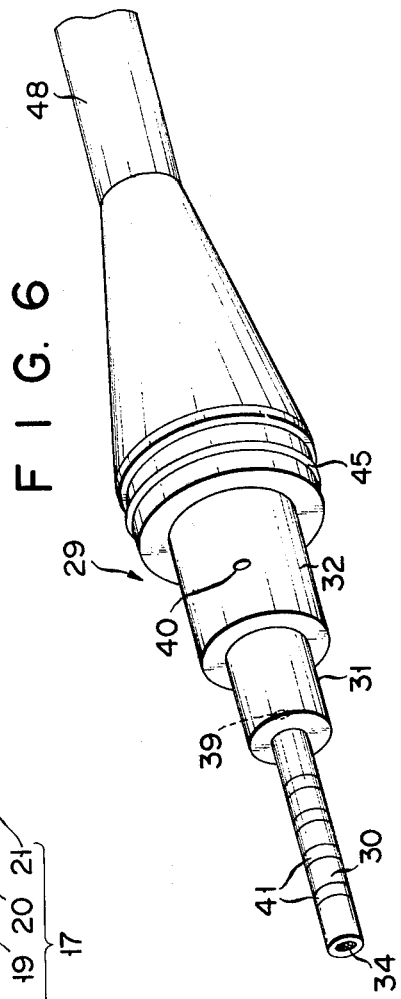

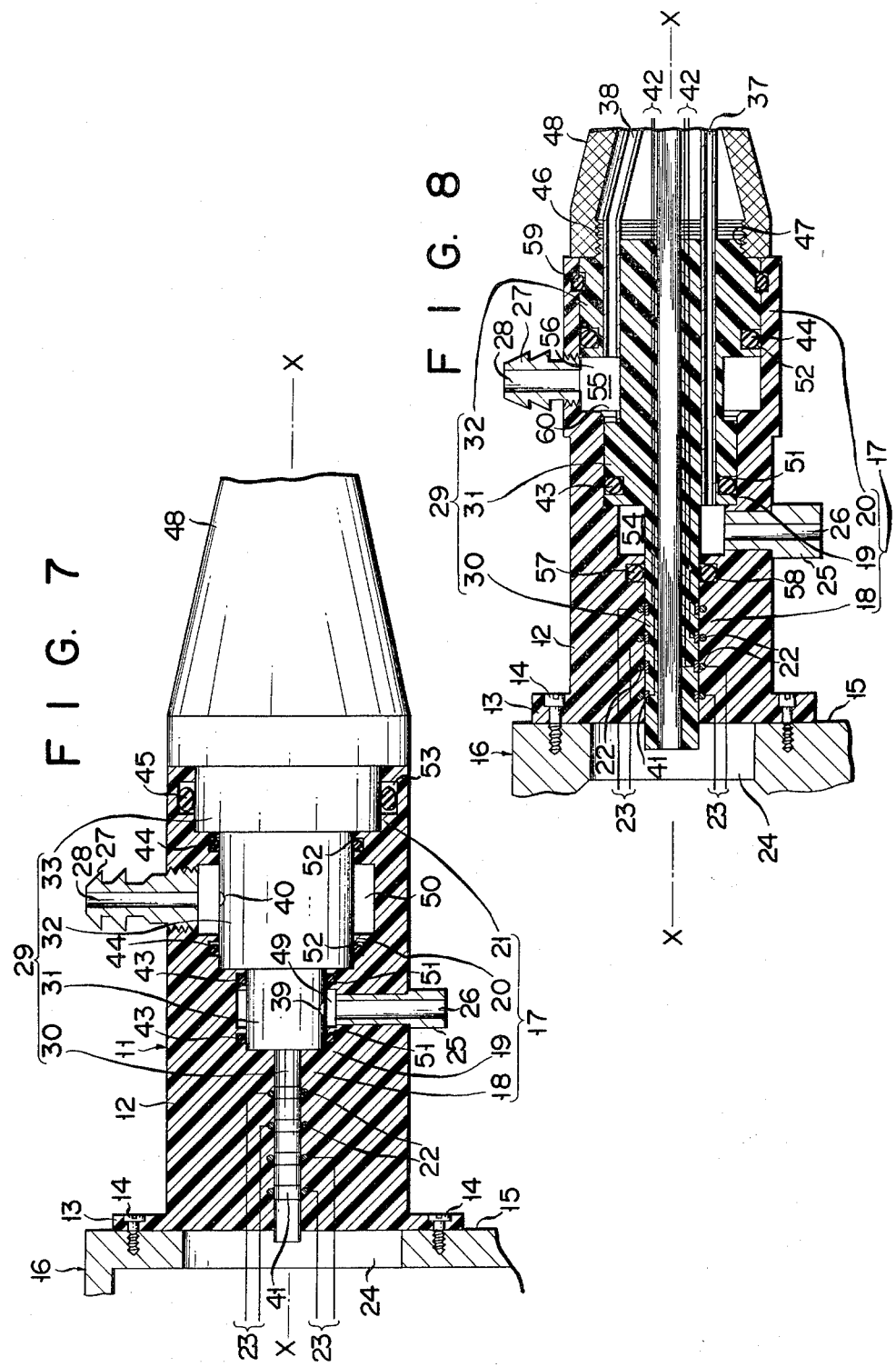

ENDOSCOPE CONNECTOR

BACKGROUND OF THE INVENTION

This invention relates to an endoscope connector which connects an endoscope-operating section to a light source, power source, fluid feeding device and suction device provided outside of an endoscope, without causing the twist of a protection tube extending between the endoscope-operating section and a connector, while the endoscope is used in the coeliac cavity.

With an endoscope in general use, a connector 4 is fitted, as shown in FIG. 1, to the free end of a flexible protection tube 3 extending from the operation section 1 of an endoscope 2. Power supply cords, illumination optical fiber bundle, fluid-feeding tube and suction tube extending from the operation section 1 through the protection tube 3 are connected by the connector 4 to the corresponding power source, light source, fluid-feeding device and suction device, thereby effecting the supply of power, light and fluid to the endoscope. With the prior art connector 4, pins 5 connected to electric cords and the distal end portion of an optical fiber bundle tube 6 into which the distal end portion of an illumination optical fiber bundle is inserted are projectively provided, as shown in FIG. 2, at the free end of the endoscope connector 4. A fitting 7 of a fluid-feeding device and a fitting 8 of a suction device are also projectively provided on the peripheral wall of the connector 4. When the connector 4 is inserted into the socket member a common console to the sources of light and power, a power cable is connected to the power source, and the illumination optical fiber bundle is connected to the light source. The fluid feeding fitting 7 and suction fitting 8 are respectively connected to a fluid-feeding device and a suction device through the corresponding connection tubes.

Where an endoscope 2 (for example, a colonofiberscope) is progressively inserted into a coeliac tubular member such as the large intestines which are intricately twisted, it sometimes happens that the endoscope 2 (colonofiberscope) has to be rotated around its axis. Where, however, the prior art endoscope connector 4 is connected to the common console to the sources of light and power, the protection tube 3 is twisted, by the rotation of the endoscope 2, because the conventional endoscope connector 4 lacks, as seen from its indicated arrangement, a member rotatable relative to the console. If the protection tube 3 is twisted excessively or frequently, the difficulties will arise that the optical fiber bundle, fluid feeding tube and suction tube are also distorted, probably resulting in breakage. The customary practice to avoid such difficulties is to pull the connector 4 out of the console socket when the protection tube 3 has been twisted to a certain extent, take the connection tubes off the fluid-feeding fitting 7 and suction fitting 8, release the protection tube 3 from distortion, insert the connector 4 again into the console socket, and attach connection tubes to the fluid-feeding fitting 7 and suction fitting 8. Therefore, the application of an endoscope (for the examination of, for example, the large intestines) has unavoidably to be interrupted, while the connector 4, fluid feeding connection tube and suction connection tube are taken off and fitted once more, thus giving rise to the disadvantage of unduly protracting a patient's pain.

SUMMARY OF THE INVENTION

The object of this invention is to provide an endoscope connector which comprises a rotatable plug member rotatable with a protection tube extending from an endoscope to the coeliac cavity, thereby preventing the twist of the parts received in the protection tube, in case the endoscope is rotated during its application in the coeliac cavity and the resultant damage or breakage of the parts, and consequently making it unnecessary to remove the endoscope connector and fluid-feeding connection tube and suction connection tube from the cammon console to the sources of light and power, thus dispensing with the operation steps required for the prior art endoscope connector and consequently reducing operation time.

According to this invention, there is provided an endoscope connector which comprises a socket member which has a cylindrical penetrating bore, that portion of said socket member at which one end of the penetrating bore is opened being connected to a console containing a light source and a connection for an electric source, and whose peripheral wall is provided with a fluid-feeding fitting and suction fitting; a cylindrical plug member which is sealingly inserted into the cylindrical penetrating bore of the socket member to rotate around the axis, receives the distal end portion of an illumination optical fiber bundle, fluid feeding tube and suction tube extending from an endoscope, said plug member having one end which is near the other end of the socket member and to which the free end of a protection tube receiving the illumination optical fiber bundle, fluid-feeding tube and suction tube is fixed; and a pair of annular chambers which are formed between the surface of the cylindrical penetrating bore of the socket member and the peripheral surface of the flug member, and one of which communicates with the fluid-feeding fitting and fluid-feeding tube, and the other of which communicates with the suction fitting and suction tube.

The plug member rotates together with the illumination optical fiber bundle, fluid-feeding tube and suction and the protection tube enclosing these members jointly with the turn of the endoscope, offering the advantage of suppressing the twist of the protection tube and its contents.

BRIEF DESCRIPTION OF THE DRAWING

This invention can be fully understood from the following detailed description with reference to the accompanying drawings in which:

FIG. 1 shows an endoscope provided with the prior art endoscope connector;

FIG. 2 is an oblique view of the prior art endoscope connector;

FIG. 3 is an oblique view of the socket member of an endoscope connector according to one embodiment of this invention connected to a console of a light source and a connection for an electric source;

FIG. 4 is an oblique view of a plug member which is to be fitted into the socket member of FIG. 3;

FIG. 5 is a longitudinal cross-sectional view of an endoscope connector according to the first embodiment of this invention;

FIG. 6 is an oblique view of a plug member included in an endoscope connector according to a second embodiment of the invention;

FIG. 7 is a longitudinal cross-sectional view of an endoscope connector using the plug member of FIG. 6; and FIG. 8 is a longitudinal cross-sectional view of an endoscope connector according to third embodiment of the invention.

DETAILED DESCRIPTION OF THE PREFERRED EMBODIMENTS

An endoscope connector according to a first embodiment of this invention comprises, as shown in FIGS. 3 and 5, a socket member 11 prepared from hard and electrically non-conductive synthetic resin such as polyamide resin or polyethelene resin. The socket member 11 comprises a hollow cylindrical body 12 and a flange 13 provided at one end of the body 12. The socket member 11 is fixed at the flange 13 to the front panel 15 of a console to the sources of light and electric power by screws 14. The cylindrical body 12 of the socket member 11 has a concentric cylindrical penetrating bore 17. This penetrating bore 17 is defined by concentric stepped regions, that is, a smallest inner diameter section 18 open at the end of the socket body 12 on which the flange 13 is provided, a medium inner diameter section 19 constituting the intermediate part of the socket body 12, a larger inner diameter section 20 adjacent to the medium inner diameter section 19 and a largest inner diameter section 21 open at the other end of the socket body 12 (FIG. 5). An even number of ring-shaped contacts 22 made of electric conductive material such as copper are embedded in the inner wall of the smallest inner diameter section 18 in a state axially spaced from each other, with the inner edge of each contact 22 exposed from the inner surface. Lead wires 23 each connected at one end to the corresponding contact 22 are extended in the socket body 12 toward said one end thereof and pass through an opening 24 formed in the front panel 15 of the console 16 and surrounded by the flange 13 up to an electric power source (not shown) connected to its connection in the console 16.

A suction fitting 25 is projectively fitted to the peripheral wall of that portion of the socket body 12 which constitutes the medium inner diameter section 19. The passage 26 of the suction fitting 25 communicates with the medium inner diameter section 19. Connected to the suction fitting 25 is the free end of a flexible suction connection tube (not shown) extended from a suction device (not shown).

A fluid-feeding fitting 27 is projectively fitted to the peripheral wall of that pertion of the socket boyd 12 which constitutes the larger inner diameter section 20. The passage 28 of the fluid-feeding fitting 27 communicates with the larger inner diameter section 20 of the socket body 12. Connected to the fluid-feeding fitting 27 is the free end of a flexible fluid-feeding connection tube (not shown) extended from a fluid-feeding device (not shown).

As shown in FIGS. 4 and 5, the endoscope connector comprises a cylindrical plug member 29 which is inserted into the socket member 11. The plug member 29 is made of the same material as the socket member 11 and is formed of a smallest outer diameter section 30, medium outer diameter section 31, larger diameter section 32 and largest outer diameter section 33 respectively engageable with the smallest inner diameter section 18, the medium diameter section 19, the larger inner diameter section 20, and the largest inner diameter section 21 of the socket body 12. An illumination optical fiber bundle 34 extended from the operation section of the endoscope penetrates the central part of the plug member 29. The distal end of the illumination optical fiber bundle 34 faces a light source (not shown) in the console 16.

An annular groove 35 is formed in the peripheral wall of the medium outer diameter section 31 of the plug member 29. This groove 35 communicates with the passage of 26 of the suction fitting 25. An annular groove 35 is also formed in the peripheral wall of the larger outer diameter section 32 of the plug member 29. The groove 36 communicates with the passage 28 of the fluid-feeding fitting 27.

A suction tube 37 extended from the operation section of the endoscope extends from that end of the plug member 29 which lies on the side of the largest outer diameter section 33 of the plug member 29 to the annular groove 35 in the plug member 29 and communicates with the groove 35 through an opening 39. A fluid-feeding tube 38 extended from the operation section of the endoscope extends from that end of the plug member 29 which lies on the side of the largest outer diameter section 33 of the plug member 29 to the annular groove 36 and communicates with the groove 36 through an opening 40.

Fluid such as carbon dioxide gas, oxide gas or other gas, or distilled water or medical solution is conducted from the fluid-feeding device to the body cavity such as the large intestine through the fluid-feeding tube 38. Through the suction tube 37, the fluid such as the gas, blood, mucus and used medical solution is conducted from the body cavity such as the great intestine to the suction device.

Embedded in the inner wall of the smallest outer diameter section 30 of the plug member 29 are annular contacts 41 always in contact with the ring-shaped contacts 22 formed in the socket member 11. Lead wires 42 extend from the contacts 4 through the plug member 29 and protrude from that end of the plug member 29 which lies on the side of the largest outer diameter section 33 up to the electrically operated respective parts such as a camer flashing device housed in the operation section of the endoscope. A pair of annular grooves 31a are formed in those portions of the peripheral wall of the medium outer diameter section 31 of the plug member 29 which lie on both sides of the annular groove 35. A pair of annular grooves 32a are formed in those portions of the peripheral wall of the larger outer diameter section 32 of the plug member 29 which lie on both sides of the annular groove 36. An annular groove 33a is formed in the peripheral wall of the largest outer diameter section 33 of the plug member 29. A region defined between the inner surface of the socket member 11 and the outer surface of the plug member 29 is sealed in a state preventing fluid leakage.

External screw threads 46 are formed on the free end of the largest outer diameter section 33 of the plug member 29. Engaged with the external screw threads 46 are internal screw theads 47 formed in one end portion of a flexible protection tube 48 enclosing a bundle of electric cords wrapping the lead wires 42, the illumination optical fiber bundle 34, the suction tube 37 the fluid-feeding tube 38. The other end of the protection tube 48 is fixed to the operation section of the endoscope. The protection tube 48 is connected to the plug member 29 by means of the external and internal screw threads 46, 47.

In operation, the endoscope connector whose plug member 29 is connected to the protection tube 48 as shown in FIG. 5 is fixed at the flange 13 of the socket member 11 to the front panel of the console 16 by the screw threats 14. The suction fitting 25 and fluid-feeding fitting 27 are inserted into the corresponding connection tubes extended from the suction device and fluid-feeding device respectively. The endoscope is inserted into a coeliac tubular member such as the large intestines which are to be examined or undergo a medical treatment. Where the endoscope is rotated about its axis while passing through the intricately twisted portions of the coeliac tubular member, the protection tube 48 is jointly rotated about its axis. As the protection tube 48 is rotated, the plug member 29 are also rotated about its axis X—X through substantially the same angle as the endoscope. Even if, therefore, the endoscope is rotated frequently in the same direction or very often in various directions, the protection tube 48 and plug member 29 are rotated together easily and smoothly. Consequently, the protection tube 48 is saved from twisting, thus preventing the illumination optical fiber bundle 34, suction tube 37, fluid-feeding tube 38 and electric cords received in the protection tube 48 from being twisted, entangled with each other, damaged or broken.

Further, when the plug member 29 is rotated, the annular contacts 41 in the smallest outer diameter section 30 of the plug member 29 always slidably contact the ring-shaped contacts 22 in the smallest inner diameter section 18 of the socket member 11. Therefore, the electric power source and the lead wires 42 of the plug member 29 are always electrically connected together through the connection in the console 16. Further, the passage 26 of the suction fitting 25 and the passage 28 of the fluid-feeding fitting 27 always respectively communicate with the suction tube 37 and fluid-feeding tube 38 through the corresponding annular grooves 35, 36. No matter, therefore, how often and much the connector of the endoscope is rotated during the application of the endoscope, it is quite unnecessary to remove the connector from the console 16 or pull the suction connection tube from the suction fitting 25 and the fluid-feeding connection tube from the fluid-feeding fitting 27, thus elevating the operation efficiency of an endoscope.

FIGS. 6 and 7 show an endoscope connector according to a second embodiment of this invention. With this second embodiment, the annular groove 35 formed in the peripheral wall of the medium outer diameter section 31 of the plug member 29 of the first embodiment and the annular groove 36 formed in the peripheral wall of the larger diameter outer section 32 of the plug member 29 are respectively replaced by an annular groove 49 formed in the inner face of the medium inner diameter section 19 of the socket member 11 and an annular groove 50 formed in the inner face of the larger diameter inner section 20 of the socket member 11. Instead, O-rings 43, 44, 45 are inserted into the annular grooves 51, 52, 53 respectively formed in the inner walls of the medium diameter inner section 19, larger inner diameter section 20 and largest inner diameter section 21 of the socket member 11. The other part of the second embodiment has the same construction as that of the first embodiment and the same function (description thereof being omitted).

With an endoscope connector of FIG. 8 according to a third embodiment of this invention, the annular grooves 49, 50 of the second embodiment are replaced by an annular groove 54 formed in the smallest inner diameter section 18 of the socket member 11 adjacent to the medium inner diameter section 19 of the socket member 11, and an annular chamber 55 defined by an annular groove 56 between the forward end of the medium inner diameter section 19 and the rear end of the larger inner diameter section 20 of the socket member 11 and an annular groove 60 formed in the outer wall of the rear end portion of the larger outer diameter section 32 of the plug member 29. The annular groove 54 communicates with the suction tube 37, and the annular chamber 55 communicates with the fluid-feeding tube 38. An annular groove 57 is formed in the inner wall of the smallest inner diameter section 18 of the socket member 11. An O-ring 58 placed in the annular groove 57 effects a sealing between the smaller inner diameter section 18 of the socket member 11 and the smaller outer diameter section 30 of the plug member 29. An O-ring 59 is formed between the regions lying near the free ends of the socket member 11 and plug member 29 to seal both members. The endoscope connector of the third embodiment does not include a largest outer and inner diameter sections of other embodiments but has substantially the same construction as the second embodiment in other respects.

The combination of the annular grooves 35, 36 and the inner surface of the socket member 11, the combination of the annular grooves 49, 50 and the outer surface of the plug member 29, and the annular chamber 55 constitute annular communication chambers for establishing communication between the suction fitting 25 and suction tube 37 and also communication between the fluid-feeding fitting 27 and fluid-feeding tube 38.

The parts of the second and third embodiments which are the same as or similar to those of the first embodiment are denoted by the same numerals, description thereof being omitted.

What is claimed is:

1. In an endoscope having an operation section; an illumination optical fiber bundle, a fluid-feeding tube and a suction tube extending from said operation section; and endoscope connector connected to a console disposed externally of said endoscope and including a light source and a connection to an electric power source, said endoscope connector having a fluid-feeding fitting connected to said fluid-feeding tube and a suction fitting connected to said suction tube; and a protection tube surrounding said illumination optical fiber bundle, said fluid-feeding tube and said suction tube and having two ends, one end thereof being connected to said endoscope connector and the other end thereof being connected to said operation section, the improvement wherein said endoscope connector comprises:
a socket member comprising a socket body having a generally cylindrical bore penetrating therethrough and having two ends and said fluid-feeding and suction fittings mounted on said socket body, said socket member being connected to said console at a portion of said socket body to which one of said two ends of said bore opens;
a generally cylindrically plug member rotatably and sealingly inserted in said socket body and having two ends, said plug member having said illumination optical fiber passing therethrough and allowing both said fluid-feeding tube and said suction tube to extend therein from one of said two ends of the plug member which is remote from said one of said two ends of said bore and to which said other end of said protection tube is connected; and a pair of annular communication chambers defined between said socket body and said plug member to surround said plug member, one of said communication chambers being adapted to establish communication between said fluid-feeding fitting and said fluid-feeding tube and the other communication chamber being adapted to establish communication between said suction fitting and said suction tube, respectively.

2. The endoscope connector according to claim 1, wherein said communication chambers are defined between said socket member and the annular grooves formed in said plug member.

3. The endoscope connector according to claim 1, wherein said communication chamber are defined between said plug member and said annular grooves formed in the socket member.

4. The endoscope connector according to any one of the claims 1 to 3, wherein ring-shaped contacts are formed in the socket member so as to exposed to said bore in a state spaced from each other axially of said bore; lead wires are extended from said ring-shaped contacts in said socket member to protrude from said one of said two ends of said socket member for connection to said connection in said console; annular contacts are formed in an outer surface of said cylindrical plug member always in contact with the corresponding ring-shaped contacts; and the lead wires are extended from the corresponding annular contacts in said plug member to project from said one of said two ends of said plug member into said operation section of said endoscope.

5. The endoscope connector according to claim 1, wherein said socket body comprises a smallest inner diameter section, a medium inner diameter section and larger inner diameter section concentrically arranged in series; and said plug member comprises a smallest outer diameter section, a medium outer diameter section and a larger outer diameter section respectively having substantially the same inner diameters as the corresponding smaller inner diameter section, medium inner diameter section and larger inner diameter section of said socket member.

6. The endoscope connector according to claim 5, wherein said one of said communication chambers in formed in said medium outer diameter section of said plug member, and said other communication chamber is formed in said larger outer diameter section of said plug member.

7. The endoscope connector according to claim 5, wherein said one of said communication chambers is formed in said medium inner diameter section of said socket member, and said other communication chamber is formed in said larger inner diameter section of said socket member.

8. The endoscope connector according to claim 5, wherein said one of said communication chambers is defined by said larger inner diameter section of said socket member and an annular groove formed between said medium outer diameter section and larger outer diameter section of said plug member; and the other communication chamber is defined by an annular groove formed in said smaller inner diameter section of said plug member which is formed adjacent to said medium outer diameter section of said plug member, and said smaller inner diameter section of said socket member.

9. The endoscope connector according to any one of claims 5 to 8, wherein annular contacts are formed in an outer surface of said plug member in a state spaced from each other axially of said plug member; lead wires are extended from the corresponding annular contacts through the plug member to project from said one of said two ends of the plug member into said operation section of the endoscope; ring-shaped contacts are formed in an inner surface of the smallest inner diameter section of the socket member always in contact with the corresponding annular contacts; and lead wires are extended from the corresponding ring-shaped contacts through said socket member to project from said one of said two ends of the socket member to said connection in said console.

* * * * *